US012714440B2

(12) United States Patent
Suh et al.

(10) Patent No.: US 12,714,440 B2
(45) Date of Patent: Aug. 25, 2026

(54) IMPLANT DRILL

(71) Applicant: DENTIUM CO., LTD., Gyeonggi-do (KR)

(72) Inventors: Seung-Woo Suh, Gyeonggi-do (KR); Byunggyu Song, Gyeonggi-do (KR); Sung Min Chung, Gyeonggi-do (KR)

(73) Assignee: DENTIUM CO., LTD., Gyeonggi-do (KR)

( * ) Notice: Subject to any disclaimer, the term of this patent is extended or adjusted under 35 U.S.C. 154(b) by 126 days.

(21) Appl. No.: 18/410,648

(22) Filed: Jan. 11, 2024

(65) Prior Publication Data

US 2025/0228570 A1 Jul. 17, 2025

(51) Int. Cl.
*A61B 17/16* (2006.01)

(52) U.S. Cl.
CPC ................................ *A61B 17/1615* (2013.01)

(58) Field of Classification Search
CPC . A61B 17/16; A61B 17/1613; A61B 17/1615; A61B 17/1262; A61B 17/1622; A61B 17/1624; A61B 17/1626; A61B 17/1628; A61B 17/1673; A61C 8/0089; A61C 8/0092
See application file for complete search history.

(56) References Cited

U.S. PATENT DOCUMENTS 9,022,783 B2 * 5/2015 Huwais .............. A61B 17/1604 433/165
9,326,778 B2 * 5/2016 Huwais .............. A61B 17/1615
10,980,548 B2 * 4/2021 Huwais .............. A61B 17/1673
12,076,212 B1 * 9/2024 Alruhaimi .......... A61B 17/1615
12,419,651 B2 * 9/2025 Kim .................. A61B 17/1673
2005/0203526 A1 * 9/2005 Ellis ........................ B23B 51/00 606/80
2006/0210949 A1 * 9/2006 Stoop ................ A61B 17/1673 433/165
2009/0136898 A1 * 5/2009 Kim ..................... A61C 8/0092 433/165
2009/0142731 A1 * 6/2009 Kim ..................... A61C 8/0092 433/165
2013/0218160 A1 * 8/2013 Bjorn ................ A61B 17/1615 606/80

(Continued)

FOREIGN PATENT DOCUMENTS

CN 221786706 U * 10/2024
JP 2003245283 A * 9/2003 ......... A61B 17/1615

(Continued)

OTHER PUBLICATIONS

WIPO English machine translation of JP2003245283.*

*Primary Examiner* — Eric S Gibson
(74) *Attorney, Agent, or Firm* — Secant, IP PLLC; Jay S. Franklin

(57) ABSTRACT

An implant drill according to the present invention includes: a drill body having a threaded cutting edge formed on an outer circumference thereof; and a reverse flute formed in a form of a groove on an outer circumference of the drill body so that cut bone chips are collected, and having a rotational direction and reverse directionality of the drill body so that the collected bone chips are pushed toward an end portion entering an inside of a drilling hole of the drill body by a rotation of the drill body.

20 Claims, 6 Drawing Sheets

(56) References Cited

U.S. PATENT DOCUMENTS

| | | | | |
|---|---|---|---|---|
| 2014/0045141 | A1* | 2/2014 | Chen | A61C 1/087 433/83 |
| 2015/0342709 | A1* | 12/2015 | Huwais | A61C 8/0089 433/173 |
| 2016/0128810 | A1* | 5/2016 | Fostick | G16Z 99/00 703/1 |
| 2017/0071704 | A1* | 3/2017 | Huwais | A61C 1/0061 |
| 2018/0281085 | A1* | 10/2018 | Leblanc | A61B 17/1673 |
| 2019/0029695 | A1* | 1/2019 | Huwais | A61B 17/1673 |
| 2019/0150953 | A1* | 5/2019 | Budyansky | A61B 17/1637 |
| 2021/0386513 | A1* | 12/2021 | Kofron | A61C 3/02 |
| 2023/0301696 | A1* | 9/2023 | Kim | A61C 8/0018 |
| 2023/0404705 | A1* | 12/2023 | Kim | A61C 1/084 |
| 2024/0398516 | A1* | 12/2024 | Hernández Suarez | A61C 8/0089 |
| 2025/0228570 | A1* | 7/2025 | Suh | A61B 17/1615 |

FOREIGN PATENT DOCUMENTS

| | | | | |
|---|---|---|---|---|
| KR | 20120130513 | A * | 12/2012 | A61B 17/1673 |
| KR | 20240126229 | A * | 8/2024 | A61B 17/1604 |
| KR | 20250103423 | A * | 7/2025 | A61B 17/8894 |
| WO | WO-2004014241 | A1 * | 2/2004 | A61B 17/1615 |
| WO | WO-2017124079 | A1 * | 7/2017 | A61B 17/1673 |
| WO | WO-2018017577 | A1 * | 1/2018 | A61B 17/32 |
| WO | WO-2018071863 | A1 * | 4/2018 | A61B 17/1617 |
| WO | WO-2020161511 | A1 * | 8/2020 | A61C 8/0089 |
| WO | WO-2021020656 | A1 * | 2/2021 | A61B 17/1673 |
| WO | WO-2022124690 | A1 * | 6/2022 | A61C 8/0092 |
| WO | WO-2024172261 | A1 * | 8/2024 | A61B 17/1604 |

* cited by examiner

IMPLANT DRILL

BACKGROUND

1. Field

The present invention relates to an implant drill.

2. Description of Related Art

As we enter an aging society in earnest, interest in medical technologies that can solve maintenance, treatment, or the like of health is increasing. In addition to orthopedic surgery closely related to bone health which is gaining prominence as we enter an aging era, dental implant treatments are also increasing.

When it is difficult to place an implant because a gum bone in a maxilla is insufficient or thin, surgery is performed to lift a lower membrane of a maxillary sinus and secure the amount of bone in a space generated by the lifting of the lower membrane (sinus bone graft). In this case, the known methods used first drill a maxillary bone, lift the lower membrane of the maxillary sinus using a tool, fill the lifted space with a bone graft material, and then place the implant into the hardened bone graft material.

It is important for the tool used for this procedure to secure stability and accuracy without damaging the membrane of the maxillary sinus in the process of making a hole in the maxilla and lifting the membrane. In addition, the key is how much the patient's discomfort and the possibility of side effects caused by the artificial bone graft material that is filled in the space generated by lifting the membrane can be reduced.

SUMMARY

An object of the present invention provides an implant drill in which bone chips are cut according to a rotation of a drill body to be collected and pushed to an end portion of the drill body, the collected bone chips lift a membrane of the maxillary sinus, and the cut bone chips may be naturally filled in a space where the cut bone chips are lifted.

Another object of the present invention provides a drill design capable of securing a space where a bone chip may be accommodated while forming a separate cutting means so that a drill body may easily penetrate into an alveolar bone.

The problems of the present invention are not limited to those mentioned above, and other technical problems will be clearly understood by those skilled in the art from the following description.

According to an aspect of the present invention, an implant drill includes: a drill body having a threaded cutting edge formed on an outer circumference thereof; and a reverse flute formed in a form of a groove on an outer circumference of the drill body so that cut bone chips are collected, and having a rotational direction and reverse directionality of the drill body so that the collected bone chips are pushed toward an end portion entering an inside of a drilling hole of the drill body by a rotation of the drill body.

The reverse flute may be formed in a spiral shape having a pitch greater than that of the threaded cutting edge.

The reverse flute may be formed straight.

A plurality of reverse flutes may be arranged radially along a circumferential direction of the drill body when viewed in a plan view of the drill body.

The reverse flute may be formed to have a round transverse cross-section. As another example, the reverse flute may be formed to have a triangular or square transverse cross-section.

The reverse flute may be formed to increase in depth toward the end portion of the drill body.

The implant drill may further include a vertical cutting edge protruding from the end portion of the drill body.

The vertical cutting edge may be formed in a shape of a '1' having a left side surface and a right side surface when viewed in plan view.

The end portion of the drill body from which the vertical cutting edge begins to protrude may be formed in a flat shape.

A space portion in which bone chips are collected may be formed between the left side of the vertical cutting edge and the end portion of the drill body, and between the right side surface of the vertical cutting edge and the end portion of the drill body, respectively.

The vertical cutting edge may have a triangular profile that is sharp toward an end when viewed from the left side surface or the right side surface.

The threaded cutting edge may include a steep surface facing the end portion of the drill body and a gentle surface facing an opposite side of the end portion of the drill body.

The threaded cutting edge may have a spiral direction opposite to a rotational direction of the drill body when viewed from the side surface of the drill body.

According to another aspect of the present invention, an implant drill includes: a drill body having a cutting edge formed on an outer circumference thereof; a vertical cutting edge formed to protrude from the end portion of the drill body; and a reverse flute formed in a form of a groove on an outer circumference of the drill body so that cut bone chips are collected, and having a rotational direction and reverse directionality of the drill body so that the collected bone chips are pushed toward an end portion entering an inside of a drilling hole of the drill body by a rotation of the drill body.

DETAILED DESCRIPTION

Hereinafter, an implant drill related to the present invention will be described in detail with reference to the accompanying drawings. Terms used in the specification and claims may not be limited to dictionary meanings, and may be appropriately defined and understood to explain the present invention in the best way.

Figure 1:
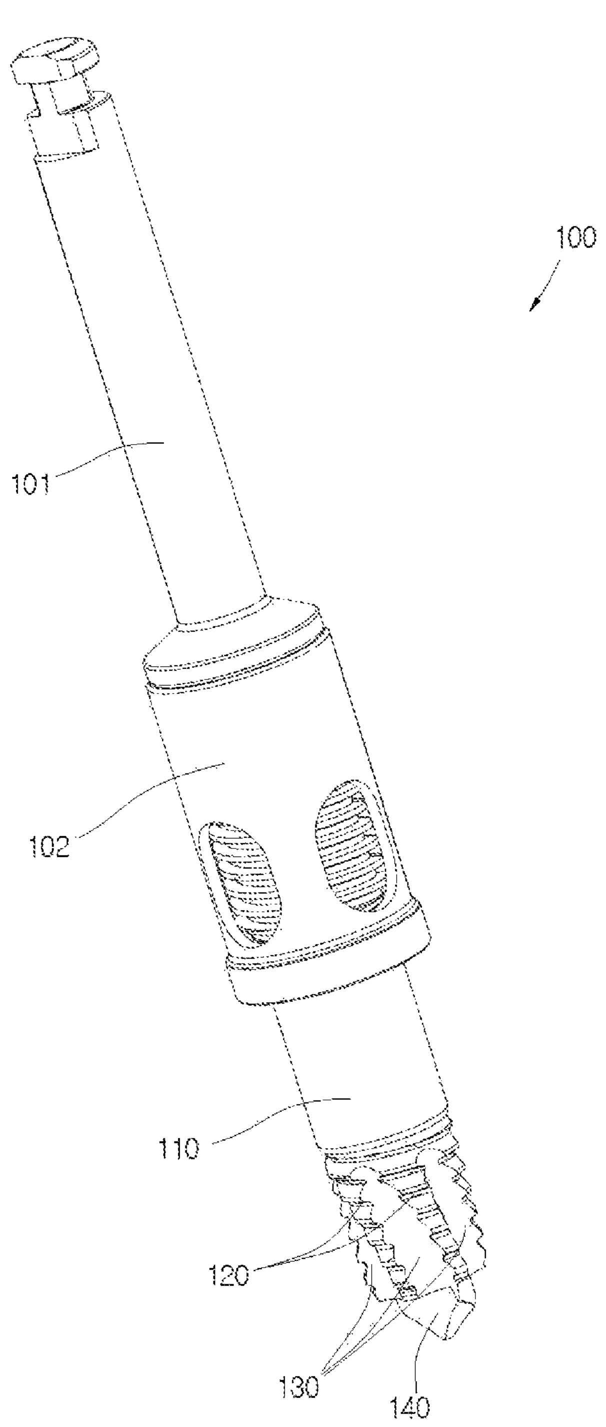
FIG. 1 is a perspective view of an implant drill according to an example of the present disclosure.

Referring to FIG. 1, the implant drill 100 may include a shank 101 for mounting a drill body 110 to a handpiece (not illustrated). A stopper 102 may be provided between the drill body 110 and the shank 101 to limit a drilling depth. However, known shapes or elements may be applied to the shank 101 and the stopper 102, and for the sake of the gist of the present invention, further detailed description is omitted.

A lower end of the drill body 110 corresponds to a cut portion for drilling an alveolar bone of a maxilla, for example. The cut portion may include a threaded cutting edge 120, a reverse flute 130, and a vertical cutting edge 140. These are illustrated in detail in FIGS. 2 to 4.

Figure 2:
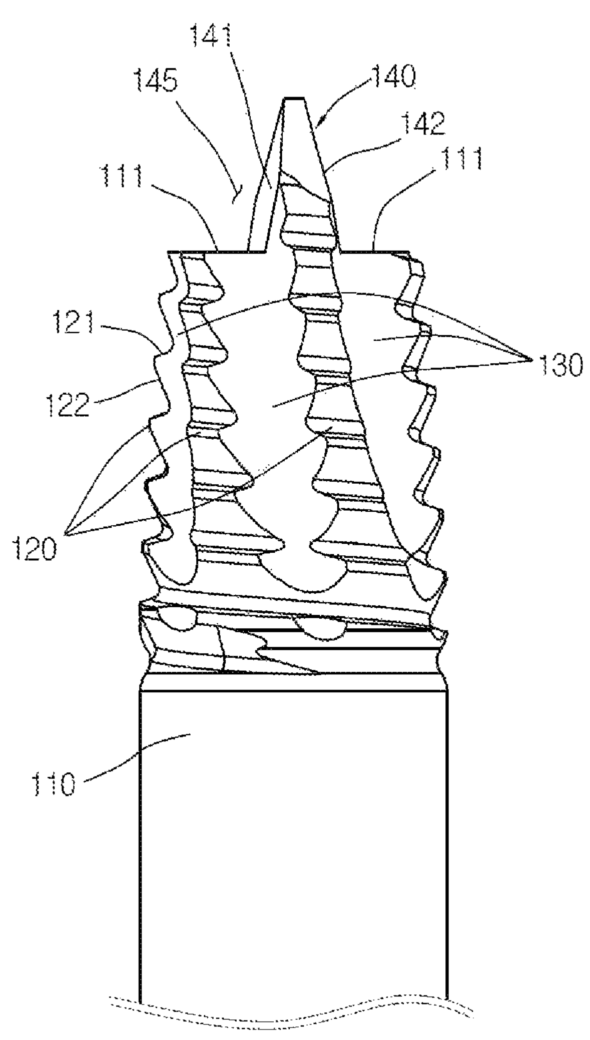
FIG. 2 is a side view centered on a cut portion of the implant drill of FIG. 1.
Figure 3:
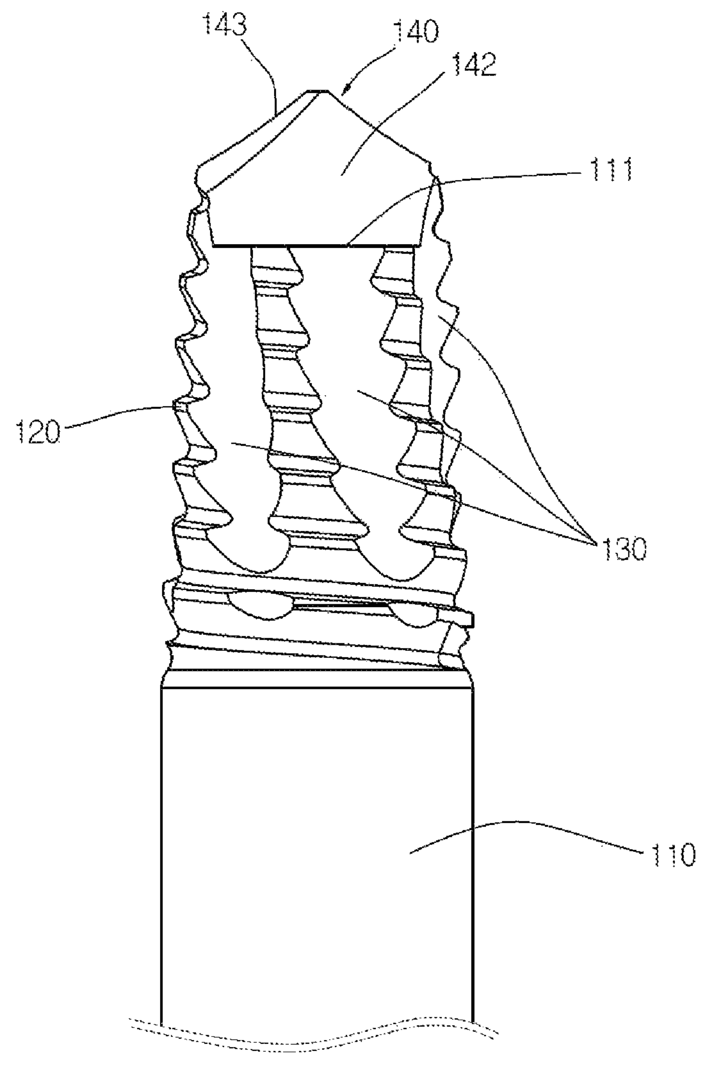
FIG. 3 is a side view illustrating the implant drill of FIG. 2 rotated 90°.

A threaded cutting edge 120 is formed in a form having a plurality of threads on an outer circumference of the drill body 110, and is capable of cutting a side wall of a hole that is drilled according to a rotation of the drill body 110. As illustrated in FIG. 2, individual threads forming the threaded cutting edge 120 may include a steep surface 121 facing an end portion 111 of the drill body 110 and a gentle surface 122 facing an opposite to the end portion 111 of the drill body 110. The threaded cutting edge 120 has a spiral direction opposite to a rotational direction (direction from the left to the right when viewed in FIGS. 2 and 3, and a counter-clockwise direction in FIG. 4) of the drill body 110 when viewed from the side of the drill body 110. Accordingly, the threaded cutting edge 120 may be a form in which the left is high and the right is low, as illustrated in FIGS. 2 and 3 when viewed from the front surface or side surface of the drill body 110.

Figure 4:
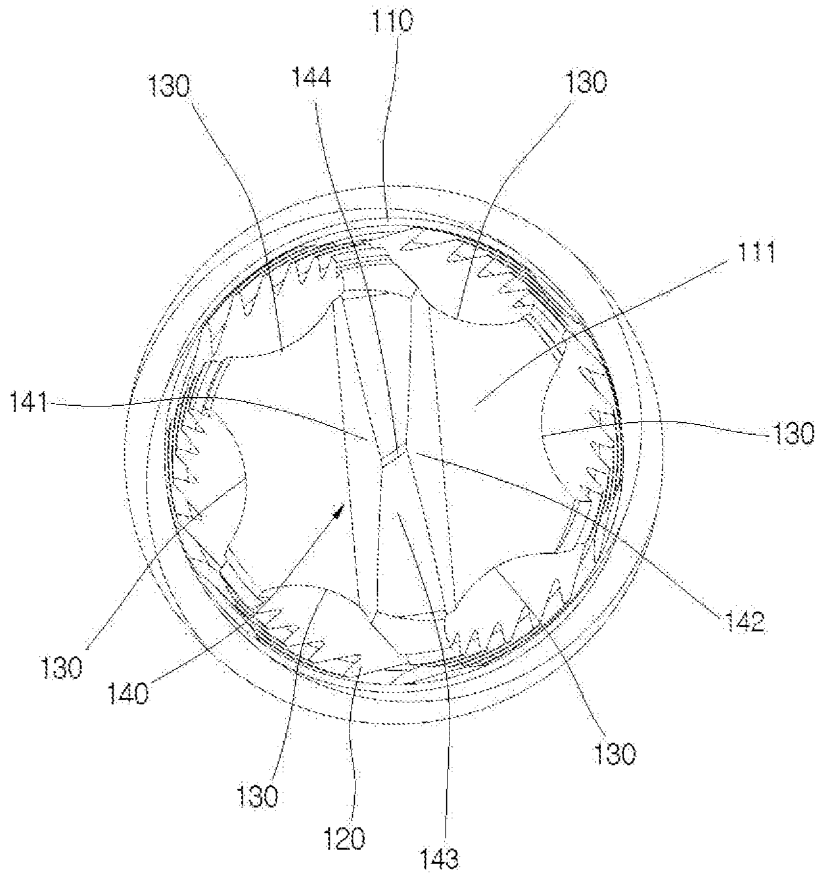
FIG. 4 is a plan view of the cut portion of the implant drill of FIG. 2.

At least one reverse flute 130 may be formed on an outer circumference of the drill body 110 along with the threaded cutting edge 120. Six reverse flutes 130 illustrated in FIGS. 2 to 4 are arranged radially when viewed in plan view. Each reverse flute 130 is in the form of a groove on the outer circumference of the drill body 110 so that cut bone chips may be collected, and is formed to have the rotational direction and reverse directionality of the drill body 110 so that the collected bone chips may be pushed to the end portion 111 entering an inside of a drilling hole of the drill body 110 by the rotation of the drill body 110 in terms of the direction.

The reverse flute 130 may be formed in a spiral shape having a pitch greater than that of the threaded cutting edge 120. However, the reverse flute 130 can also be formed straight at an outer circumference of the drill body 110 as long as it has the rotational direction and reverse directionality of the drill body 110.

Each reverse flute 130 may have a relatively small turn length in the section where the threaded cutting edge 120 is formed in the drill body 110. For example, as illustrated in FIGS. 2 and 3, the reverse flute 130 may have a turn length of equal to or less than ¼ along a circumferential direction of the drill body 110. However, depending on needs of design, the reverse flute 130 may have a longer or shorter turn length.

The reverse flute 130 may be in the form of a wider and deeper groove than the threaded cutting edge 120. The reverse flute 130 may be formed to increase in depth toward the end portion 111 of the drill body 110 so that the bone chips may be easily collected in the direction of the end portion 111 of the drill body 110 by the rotation of the drill body 110. The reverse flute 130 may be treated to have a smooth surface or may have a coating layer so that the bone chips may be easily pushed and moved to the end portion 111 of the drill body 110. The reverse flute 130 or the drill body 110 may be subjected to surface treatment to prevent corrosion of a metal surface.

The vertical cutting edge 140 is formed to protrude from the end portion of the drill body 110. As illustrated in FIG. 4, the vertical cutting edge 140 may be in the shape of a '1' having a left side surface 141 and a right side surface 142 when viewed in plan view. The vertical cutting edge 140 is flat when viewed from the side, as illustrated in FIG. 2, and may have a sharp triangular profile 143 toward an end when viewed from the left side surface 141 or the right side surface 142 while rotating 90° as illustrated in FIG. 3. A vertex of the triangular profile 143 may include a chisel edge 144. The vertical cutting edge 140 has a flat erect shape, and therefore, may easily penetrate into the alveolar bone.

As illustrated in FIG. 2, the end portion 111 from which the vertical cutting edge 140 of the drill body 110 begins to protrude may be flat, and a space portion 145 in which the bone chips may be collected is formed between the left side surface 141 of the vertical cutting edge 140 and the end portion 111 of the drill body 110, and between the right side surface 142 of the vertical cutting edge 140 and the end portion 111 of the drill body 110. This space portion 145 primarily serves as a space where the bone chips cut by the vertical cutting edge 140 are collected, and also serves as a space where the bone chips pushed out through the above-mentioned reverse flute 130 are collected. The bone chip filled in the space portion 145 is filled in the left and right space portions 145 of the vertical cutting edge 140 and becomes blunt, so the membrane of the maxillary sinus may be naturally lifted by the bone chip. In addition, the bone chip filled in the space portion 145 induces the force acting when the membrane of the maxillary sinus is lifted to be well distributed.

Figure 5:
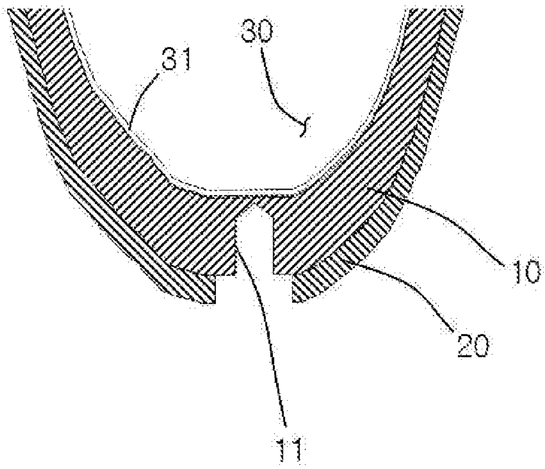
FIGS. 5 and 6 are conceptual cross-sectional views for exemplarily describing performing a sinus bone graft using the implant drill related to the present invention.

Hereinafter, the sinus bone graft (sinus lifting) using the implant drill 100 will be described with reference to FIGS. 5 and 6.

When it is difficult to place an implant because a gum bone in a maxilla is insufficient or thin, surgery is performed to lift a lower membrane of a maxillary sinus and secure the amount of bone in a space generated by the lifting of the lower membrane. For this purpose, as illustrated in FIG. 5, a drill groove 11 is primarily formed in the alveolar bone 10 and a gum 20 of the maxilla.

Figure 6:
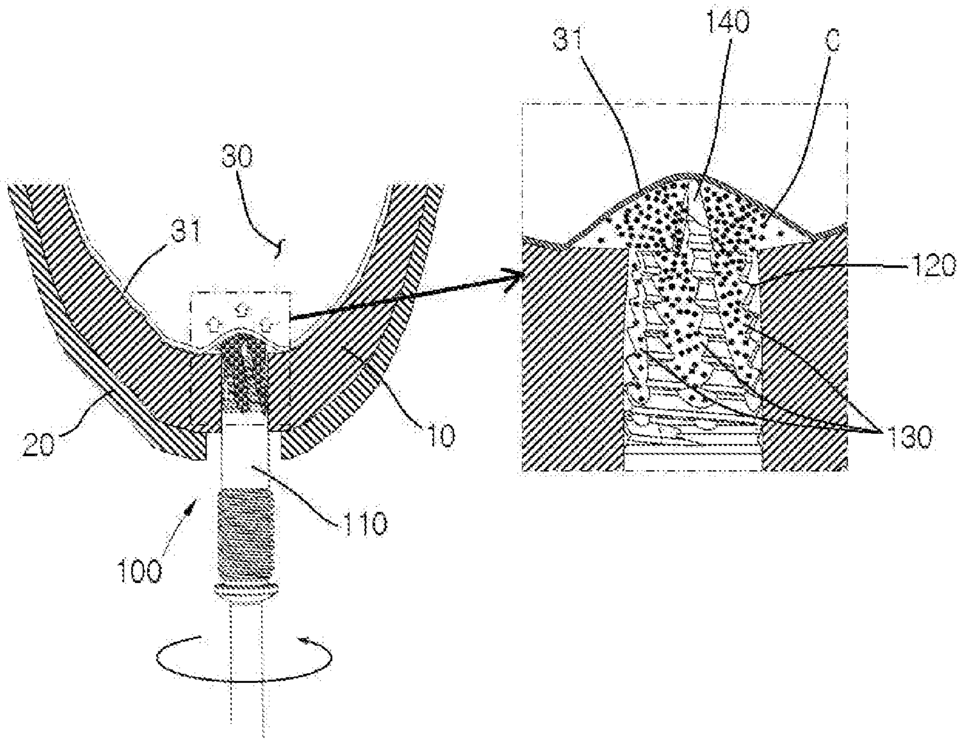

Next, as illustrated in FIG. 6, the alveolar bone 10 is drilled while widening the drill groove 11 using the implant drill 100 described above. In this process, a bone chip C generated by the threaded cutting edge 120 and the vertical cutting edge 140 (see FIGS. 2 and 3) moves toward the maxillary sinus 30 by the reverse flute 130 (see FIGS. 2 and 3), and a membrane 31 of the maxillary sinus 30 is lifted by the pressure generated by the vertical cutting edge 140 and the rise of the collected bone chip C. In other words, the bone chip C generated by the rotation of the implant drill 100 naturally acts as a pressure to lift the membrane 31. Thereafter, a process of removing the implant drill 100 and then lifting the membrane 31 wider and deeper using a separate tool (not illustrated) may be involved. In this process, the bone chip C filled in the space where the membrane 31 is lifted continues to remain and fills a cavity along with the bone graft material that will be present later. Since this method simultaneously performs drilling and harvesting of the bone chip C using the implant drill 100, the surgery may be performed as compactly as possible.

Figure 7:
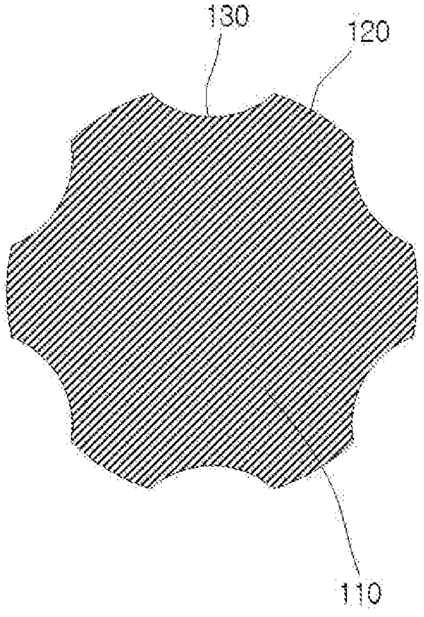
FIG. 7 is a transverse cross-sectional view of the implant drill of FIG. 2.

FIG. 7 is a transverse cross-sectional view of the implant drill of FIG. 2, and may illustrate that a plurality (6) of reverse flutes 130 are radially arranged between threaded cutting edges 120 along the circumferential direction of the drill body 110. In this example, the transverse cross-section of the reverse flute 130 has a round shape.

Figure 8:
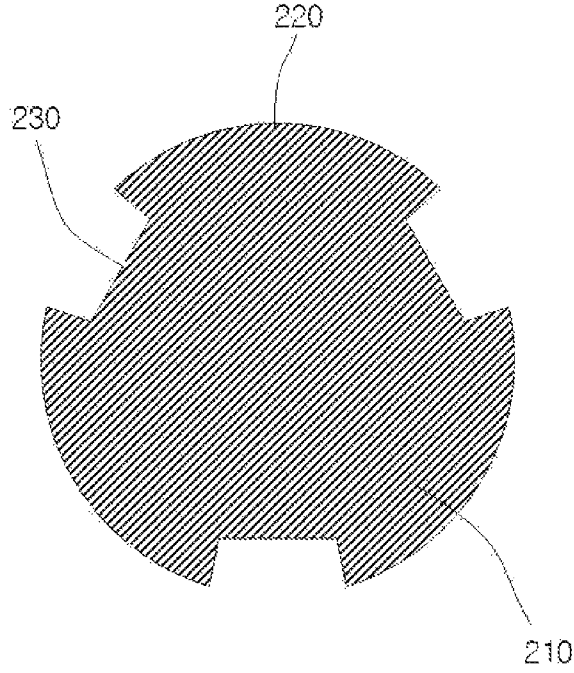
FIGS. 8 and 9 are transverse cross-sectional views of an implant drill according to another example of the present invention.

FIG. 8 is a transverse cross-sectional view of an implant drill according to another example of the present invention, in which three reverse flutes 230 are radially arranged between threaded cutting edges 220 along a circumferential direction of the drill body 210. In this example, the transverse cross section of the reverse flute 230 is formed in a square shape.

Figure 9:
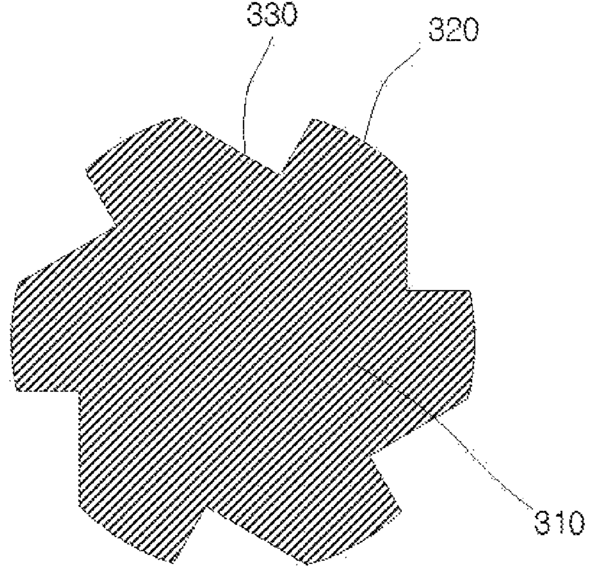

FIG. 9 is a transverse cross-sectional view of an implant drill according to another example of the present invention, in which six reverse flutes 330 are radially arranged between threaded cutting edges 320 along a circumferential direction of the drill body 310. The transverse cross section of the reverse flute 330 is formed in a triangular shape. In this case, angles of two adjacent surfaces of a triangle of each reverse flute 330 may be formed to be different from each other.

According to the implant drill according to the present invention, the reverse flute having the reverse directionality and the rotational direction of the drill body is formed on the outer circumference of the drill body where the cutting edge is formed. In this case, the bone chips generated by the rotation of the drill body are pushed toward the end portion of the drill body by the reverse flute, so the membrane of the maxillary sinus may be naturally lifted by the bone chips collected at the end portion of the drill body when the drilling hole is drilled. By causing the bone chips filled by lifting the membrane of the maxillary sinus to distribute the force acting on the membrane well, it is possible to minimize damage to the membrane. In addition, since the bone chip is naturally filled in the lifted membrane, the use of the artificial bone graft material may be reduced, and thus, the patient's discomfort and side effects due to surgery may be reduced accordingly.

According to the implant drill according to the example of the present invention, the vertical cutting edge is formed at the end portion of the drill body, so the drill may easily penetrate into the alveolar bone and the space between the vertical cutting edge and the drill body may be used as the space where the bone chips may be accommodated.

The implant drill described above is not limited to the configuration and method of the described embodiments. All or some of the respective exemplary embodiments may be selectively combined with each other so that the above-mentioned exemplary embodiments may be variously modified to substitutable equivalents.

What is claimed is:

1. An implant drill, comprising:

a drill body; and at least reverse one flute formed in a form of a groove on an outer circumference of the drill body so that cut bone chips are collected as the drill body rotates, and having a rotational direction and reverse directionality of the drill body so that the collected bone chips are pushed toward an end portion of the drill body entering an inside of a drilling hole of the drill body by a rotation of the drill body, wherein the at least one reverse flute increases in depth toward the end portion of the drill body such that a chip-receiving capacity of the at least one reverse flute increases toward the end portion to facilitate smoother inward conveyance of the bone chips into the drilling hole.

2. The implant drill of claim 1, wherein the at least one reverse flute is formed in a spiral shape.

3. The implant drill of claim 1, wherein the at least one reverse flute is formed straight.

4. The implant drill of claim 1, wherein a plurality of reverse flutes are arranged radially along a circumferential direction of the drill body when viewed in a plan view of the drill body.

5. The implant drill of claim 1, wherein the at least one reverse flute is formed to have a round transverse cross-section.

6. The implant drill of claim 1, wherein the at least one reverse flute is formed to have a triangular or square transverse cross-section.

7. The implant drill of claim 1, further comprising:

a vertical cutting edge protruding from the end portion of the drill body.

8. The implant drill of claim 7, wherein the vertical cutting edge is formed in a shape of a '1' having a left side surface and a right side surface when viewed in plan view.

9. The implant drill of claim 8, wherein the end portion of the drill body from which the vertical cutting edge begins to protrude is formed in a flat shape.

10. The implant drill of claim 9, wherein a space portion in which bone chips are collected is formed between the left side of the vertical cutting edge and the end portion of the drill body, and between the right side surface of the vertical cutting edge and the end portion of the drill body, respectively.

11. The implant drill of claim 10, wherein the at least one reverse flute is in communication with the space portion so that bone chips collected in the space portion are guided into the at least one reverse flute and are pushed toward an end portion entering an inside of a drilling hole of the drill body by rotation of the drill body.

12. The implant drill of claim 7, wherein the vertical cutting edge has a triangular profile that is sharp toward an end when viewed from the left side surface or the right side surface.

13. The implant drill of claim 1, wherein the drill body includes a threaded cutting edge formed on an outer circumference thereof; and wherein the threaded cutting edge includes a steep surface facing the end portion of the drill body and a gentle surface facing an opposite side of the end portion of the drill body.

14. The implant drill of claim 1, wherein the drill body includes a threaded cutting edge formed on an outer circumference thereof; and wherein the threaded cutting edge has a spiral direction opposite to a rotational direction of the drill body when viewed from a side surface of the drill body.

15. An implant drill, comprising:

a drill body having a threaded cutting edge formed on an outer circumference thereof; and a reverse flute formed in a form of a groove on the outer circumference of the drill body so that cut bone chips are collected as the drill body rotates, and having a rotational direction and reverse directionality of the drill body so that the collected bone chips are pushed toward an end portion of the drill bod entering an inside of a drilling hole of the drill body by a rotation of the drill body;

wherein the reverse flute increases in depth toward the end portion of the drill body such that a chip-receiving capacity of the reverse flute increases toward the end portion to facilitate smoother inward conveyance of the bone chips into the drilling hole.

16. An implant drill, comprising:

a drill body having a shank to be coupled to a handpiece;

a vertical cutting edge formed to protrude from an end portion of the drill body; and a reverse flute formed in a form of a groove on an outer circumference of the drill body so that cut bone chips are collected as the drill body rotates, and having a rotational direction and reverse directionality of the drill body so that the collected bone chips are pushed toward the end portion entering an inside of a drilling hole of the drill body by a rotation of the drill body, wherein a space portion in which bone chips are collected is formed between a left side surface of the vertical cutting edge and the end portion of the drill body, and between a right side surface of the vertical cutting edge and the end portion of the drill body, respectively; and wherein the reverse flute is in communication with the space portion so that the bone chips collected in the space portion are guided into the reverse flute and are pushed toward the end portion entering the inside of the drilling hole of the drill body by rotation of the drill body.

17. The implant drill of claim 16, wherein the reverse flute is formed in a spiral shape.

18. The implant drill of claim 16, wherein a plurality of reverse flutes has six reverse flutes which are arranged radially along a circumferential direction of the drill body when viewed in a plan view of the drill body.

19. The implant drill of claim 16, wherein the reverse flute is formed to have a round transverse cross-section.

20. The implant drill of claim 16, wherein the drill body includes a plurality of cutting edges at an end portion of the drill body.

* * * * *